United States Patent [19]

Loori

[11] Patent Number: 5,154,697
[45] Date of Patent: Oct. 13, 1992

[54] COLLAPSIBLE TOPICAL HYPERBARIC APPARATUS

[75] Inventor: Phillip E. Loori, Jersey City, N.J.

[73] Assignee: Topox, Inc., Denver, Colo.

[21] Appl. No.: 679,563

[22] Filed: Apr. 2, 1991

[51] Int. Cl.$^5$ .................................. A61M 37/00
[52] U.S. Cl. .................................. 604/23; 604/305; 604/308
[58] Field of Search ............... 604/23, 289, 305, 308; 128/202.12, 205.13, 205.22, 205.24, 205.26; 623/8

[56] References Cited

U.S. PATENT DOCUMENTS

| | | |
|---|---|---|
| 4,224,941 | 9/1980 | Stivala . |
| 4,328,799 | 5/1982 | LoPiano . |
| 4,474,571 | 10/1984 | Lasley . |
| 4,480,638 | 11/1984 | Schmid .................. 604/305 X |
| 4,509,513 | 4/1985 | Lasley . |
| 4,685,447 | 8/1987 | Iversen et al. .................. 623/8 X |
| 4,778,446 | 10/1988 | Jensen .................. 604/27 |
| 4,801,291 | 1/1989 | Loori . |

FOREIGN PATENT DOCUMENTS 641061 8/1950 United Kingdom ............... 604/305

OTHER PUBLICATIONS

OXYCURE, Concord Laboratories, Inc.
OXYCURE, Hospitak, Inc.

Primary Examiner—Randall L. Green
Assistant Examiner—Mary Beth O. Jones
Attorney, Agent, or Firm—Lerner, David, Littenberg, Krumholz & Mentlik

[57] ABSTRACT

A topical hyperbaric apparatus and method is disclosed for treating wounds and lesions on a patient's body. The hyperbaric apparatus includes a shell constructed of flexible plastic material which enables the shell which provides a substantially closed internal chamber to be arrangable between an expanded and collapsed configuration having a substantially reduced volume. As a result, the hyperbaric apparatus can be economically shipped to distant locations while minimizing storage requirements. The hyperbaric apparatus is expanded for use during normal application of therapeutic gases for treatment of the patient's wounds or lesions after being adhered to the patient's body using an adhesive material. The construction of the shell form plastic-like material allows the shell to be washable during patient use which is particularly pertinent when treating incontinent patients. A nylon belt having an H-shape provided with velcro-like fastening material assists in positioning and securing the hyperbaric apparatus to the patient's body. An opening provided within the belt enables viewing of that portion of the patient's body being treated through a transparent top member of the shell.

32 Claims, 4 Drawing Sheets

COLLAPSIBLE TOPICAL HYPERBARIC APPARATUS

BACKGROUND OF THE INVENTION

The present invention relates in general to a hyperbaric apparatus and, more particularly, to a topical hyperbaric apparatus for medical treatment which is collapsible to facilitate storage and portability, as well as being disposable and washable, and adapted for use in connection with irregular localized portions of the human body upon expansion from its collapsed storage configuration.

Hyperbaric chambers are devices which create sealed environments for the application of therapeutic gases to hasten healing of lesions or wounds on a patient's body. The introduction of pressurized oxygen into such an encapsulated environment promotes healing of various types of lesions and wounds. Specifically, it has been discovered that the treatment of lesions and wounds with a hyperbaric chamber, in conjunction with various stimuli, promotes granulation, raises the capillary blood $p^{O2}$, elevates the Redox potential thereby suppressing and eliminating bacterial growth.

When hyperbaric chambers were first introduced they encompassed large portions of the patient's body. For instance, in Lasley, U.S. Pat. No. 4,509,513, the patient is apparently required to stand during treatment within a flexible rolled-out tubular chamber which has one open end sealed about the patient and the other open end sealed by, for example, tape after unrolling the tubular chamber about the patient's body. This requirement for standing is at times a sufficient enough reason to preclude the use of this chamber. The Lasley chamber is also constructed to encompass a large portion of the patient's body. This requires a relatively significant amount of oxygen and exposes areas of the body which do not require treatment to the negative effects of the therapeutic atmosphere, such as drying.

As time progressed, hyperbaric chambers became more sophisticated and topical hyperbaric chambers were developed. A topical hyperbaric chamber is a device which only encapsulates a small portion of the patient's body. As these devices have evolved though, it has become apparent that significant shortcomings continue to exist. These shortcomings include the failure to provide a convenient topical hyperbaric chamber which occupies minimum space for shipping and storage, a topical hyperbaric chamber which is capable of producing a hermetic seal in many applications, a topical hyperbaric chamber which is affordable, and a topical hyperbaric chamber which is washable, i.e., sterilizable, during use and ultimately disposable.

Prior to the present invention, portable hyperbaric chambers were available, but these failed to solve many of the presently addressed problems. For instance, LoPiano, U.S. Pat. No. 4,328,799, discloses a reusable, non-collapsible chamber of complex construction which treats only a small area of the patient's body and, therefore, solves the problem of unduly exposing healthy parts of the patient's body to the drying effects of the therapeutic gases. However, this chamber fails to provide adequate seals during various applications, despite the aid of an H-shaped belt secured about the patient's body and chamber. This poor sealing is significant because many of the areas of the body where such poor sealing occurs are areas which are highly susceptible to treatable lesions, such as bedsores on the buttock.

Lasley, U.S. Pat. No. 4,474,571, discloses a portable topical hyperbaric chamber similar to the LoPiano chamber.

Loori, U.S. Pat. No. 4,801,291 discloses a topical hyperbaric chamber which overcomes a number of the above-identified shortcomings and disadvantages. The Loori chamber includes a polyurethane foam shell which provides a substantially closed internal chamber having an opening to be exposed to the patient's body. An adhesive sealing material is provided on the shell about the opening for adhesively sealing the shell to the patient's body about the portion to be treated. A gas impermeable liner lines the internal chamber and makes the internal chamber substantially gas impermeable. However, it is known that the liner may have the tendency to develop leaks around its seal areas resulting in lower pressure operation than preferred.

The Loori chamber due to its construction from polyurethane foam cannot be washed or cleaned during use. This is particularly a disadvantage in cases where the patient being treated is incontinent. In addition, foam material is known to have a certain degree of memory which can result in the shell pulling away from the patient's body and thereby eliminating the seal area causing loss of the therapeutic gases and decrease in treatment effect.

There is known an Oxycure device which includes a flexible internal member made of foam material with a large hole passing through it. A plastic bag surrounds the foam member without covering one side of the hole to form a quasi-cup-like structure. The Oxycure device is further provided with a composite sleeve member including a front, multi-layer panel portion having a porous, absorbent layer adapted to contact the patient and a plastic sheet layer adapted to face the foam/plastic cup-like structure, and a rear panel portion comprising a plastic sheet. The front panel portion of the sleeve member includes an opening of the same size as the hole in the foam member. The sleeve member is slid over the front and rear faces of the cup-like structure so that the opening in the front panel portion aligns with the hole opening in the cup-like structure. Finally, the Oxycure device includes a pair of hoses which pierce in an unsecured manner the plastic sheet of the cup-like structure at the corners thereof so as to communicate with the foam member, and therefore, is a leak source. One hose is for the introduction of oxygen, while the other hose includes a pressure relief valve. Because of the porous characteristics of the front panel of the outer sleeve member of the Oxycure device, the manner in which the sleeve member is arranged and the use of a non-sealable plastic bag about the foam member, a hermetic seal is not achievable about the area being treated resulting in leakage of the treatment gases.

One common significant disadvantage and shortcoming of the aforementioned hyperbaric chambers are their physical size which greatly affects storage space and shipping costs. As hyperbaric chambers are being used on a worldwide basis, it is desirable to facilitate storage and shipment of these chambers to the greatest extent possible. As these known hyperbaric chambers are relatively large in size, the cost of shipping same is often a significant portion of the overall cost of the hyperbaric chamber.

There is known from Stivala, U.S. Pat. No. 4,224,941 a collapsible hyperbaric chamber. The chamber includes a pliable adhesive-backed pad having a central opening for framing the treatment region. A flaccid bag is secured to the top surface of the pad and is adapted to receive a treatment gas under pressure. A collar is provided about the edge of the opening inside the bag so that the gas pressure acts against the pad to insure proper sealing at the opening. Although the Stivala chamber is collapsible, its construction results in a number of disadvantages. Most significantly, the pliable adhesive-backed pad is of an extensive size which will interfere with the treatment of wounds or lesions when clustered over a small area of the patient's body. Use of the Stivala chamber is impractical, if not impossible, where there are multiple wounds or lesions in a given area as they would be covered by the adhesive-backed pad which would cause further injury to the patient.

Accordingly, there remains an unmet need for an improved portable hyperbaric chamber which is capable of being effectively applied to the less easily treatable areas of the human body, which create an effective hermetic seal thereat, and which can be easily stored and shipped at a minimum expense by virtue of its collapsible construction.

SUMMARY OF THE INVENTION

The topical hyperbaric chamber of the present invention addresses the aforementioned problems. In particular, it is an object of the present invention to provide a topical hyperbaric chamber capable of adapting to various contours of the human body. It is another object of the present invention to provide such a topical hyperbaric chamber which is convenient to use and fully portable. A further object of the present invention is to provide such a topical hyperbaric chamber at a cost which will enable wider use and, in the proper case, disposability; such disposability being a significant improvement and widely acknowledged as necessary in facilities which treat large numbers of patients. A still further object of the present invention is to provide a topical hyperbaric chamber which is collapsible for storage and shipping, while being expandable into an operative configuration for therapeutically treating wounds and lesions. A still further object of the present invention is to provide a topical hyperbaric chamber which is washable during use to maintain a sterile and clean environment, while at the same time, being of low cost so as to be disposable.

In accordance with one embodiment of the present invention, there is disclosed topical hyperbaric apparatus constructed of a shell defining a substantially closed internal chamber arrangable between an expanded and collapsed configuration, the shell having an opening therethrough communicating with the internal chamber, a ring within the internal chamber secured to the shell about the opening, the shell about the opening capable of conforming to a shaped surface of a patient's body, and gas introducing means for introducing therapeutic gases into the internal chamber for expanding the shell from a collapsed to an expanded configuration and therapeutically treating a portion of a patient's body exposed within the opening.

In accordance with another embodiment of the present invention, there is disclosed a topical hyperbaric apparatus constructed of a shell defining a substantially enclosed internal chamber arrangable between an expanded and collapsed configuration, the shell having an opening therethrough communicating with the internal chamber, sealing means about the opening for sealing the shell to a patient's body about a portion to be treated, a ring within the internal chamber secured to the shell about the opening, the ring being sufficiently flexible so as to be capable of conforming to an irregularly shaped surface of a patient's body, and gas introducing means for introducing therapeutic gases into the internal chamber for expanding the shell from a collapsed to an expanded configuration and therapeutically treating the portion of the patient's body exposed within the opening.

The present invention also provides an improved method of therapeutically treating wounds and lesions. More particularly, in accordance with this aspect of the present invention, there is disclosed a method of treating medical irregularities on a patient's body including providing a shell defining a substantially enclosed internal chamber arrangable between an expanded and collapsed configuration, the shell having an opening therethrough communicating with the internal chamber and a ring within the internal chamber secured to the internal surface of the shell about the opening affixing the shell to a patient's body about the opening by an adhesive layer provided on the external surface of the shell about the opening and by conforming the ring to a shaped surface of the patient's body, and introducing therapeutic gases into the internal chamber for expanding the shell from the collapsed to the expanded configuration and therapeutically treating the portion of the patient's body exposed within the opening.

BRIEF DESCRIPTION OF THE DRAWINGS

The above description, as well as further objects, features and advantages of the present invention will be more fully understood with reference to the following detailed description of a collapsible topical hyperbaric chamber, when taken in conjunction with the accompanying drawings, wherein.

DETAILED DESCRIPTION

Figure 1:
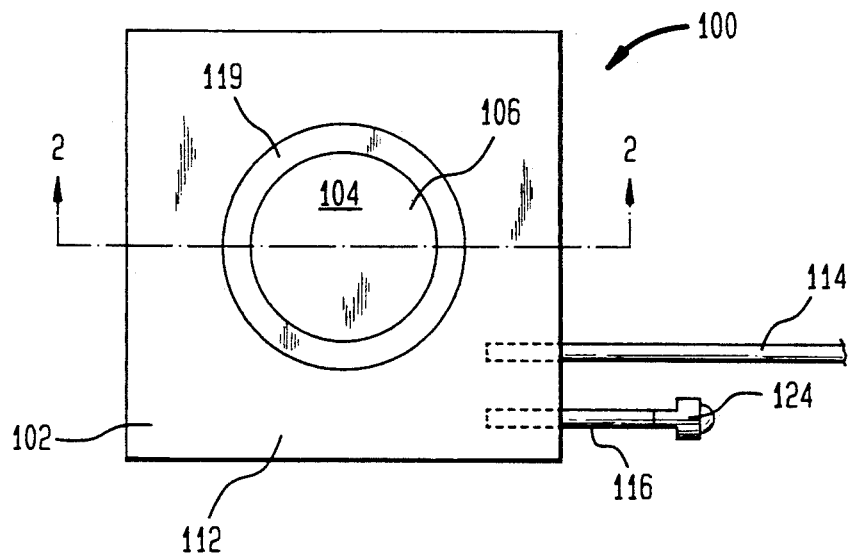
FIG. 1 is a bottom plan view of the topical hyperbaric chamber constructed in accordance with the present invention; as shown in an operative expanded configuration.
Figure 2:
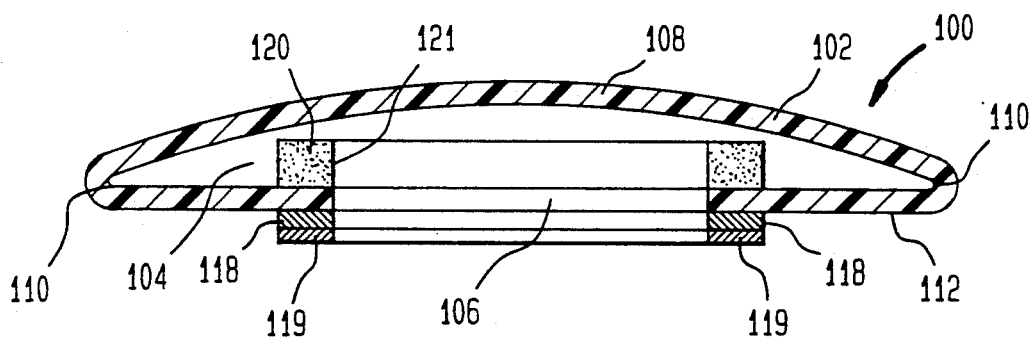
FIG. 2 is a cross-sectional view of the topical hyperbaric chamber taken along line 2—2 in FIG. 1, showing the hyperbaric chamber in a fully collapsed configuration for storage and/or shipment.

Referring now to the drawings, wherein like reference numerals represent like elements, there is shown in FIGS. 1 and 2 a preferred embodiment of a topical hyperbaric chamber constructed in accordance with the present invention and designated generally by reference numeral 100. As is conventional, the hyperbaric chamber 100 is to be applied to a patient's body for the treatment of various wounds and lesions. The hyperbaric chamber 100 administers therapeutic gases to the wound or lesion sites by creating a sealed internal chamber which encapsulates the wound or lesion sites. When thus encapsulated, therapeutic gases are introduced, and the healing of such wounds or lesions is aided.

The hyperbaric chamber 100 is constructed in the form of a shell 102 providing a substantially enclosed internal chamber 104. An enlarged opening 106 is formed within the shell 102 communicating with the internal chamber 104. The shell 102 may be constructed from a variety of suitable materials, such as resilient plastics which provide the shell with flexibility and, at the same time, allows the shell to be washed and/or sterilized during use. Washability is particularly important in treating patients who are incontinent. As plastic materials are readily available, and hence inexpensive, the hyperbaric chamber 100 is also rendered disposable after single patient treatment. Suitable plastic materials for the shell 102 include vinyl materials and the like.

The use of plastic materials also has the additional advantage in ease of fabrication of the shell 102. In this regard, the shell 102 has been depicted as being rectangular in shape in plan view. As such, the shell 102 may be formed from a pair of panel members which may be thermally joined together using heat sealing techniques. In the embodiment disclosed, the shell 102 can be constructed from a top square member 108 heat sealed circumferentially about edges 110 to a correspondingly sized square bottom member 112. In the preferred embodiment, the top member 108 is constructed from clear vinyl material for the purpose to be described hereinafter. On the other hand, the remaining components of the shell 102, i.e., bottom member 112, may be constructed from colored vinyl material such as white for aesthetic reasons. Although the shell 102 has been described as being rectangular in shape, it is to be understood that other shapes such as circular, oval and the like may be employed in accordance with the hyperbaric chamber 100 of the present invention.

A gas inlet tube 114 extends through the heat sealed edges 110 of the shell 102 and terminates within the internal chamber 104. Similarly, a pressure relief tube 116 also passes through the heat sealed edges 110 of the shell 102 and terminates within the internal chamber 104.

An adhesive sealing ring 118 is disposed directly onto the bottom member 112 of the shell 102 surrounding opening 106 and bonded thereto using a suitable adhesive. The sealing ring 118 enables adhesively sealing of the shell 102 to the patient's body to create a hermetic seal about the portion to be treated. In accordance with the preferred embodiment, the bottom member 112 extends outwardly substantially beyond the extent of the adhesive sealing ring 118. Thus, the area of the bottom wall 112 is substantially greater than the area of the adhesive sealing ring 118.

The sealing ring 118 is preferably a hydro-fluid material capable of repeated use and rejuvenation. The material of the sealing ring 118, for proper use, should also be hypo-allergenic. These characteristics are present in the adhesive material Karaya, a naturally occurring polymer resin. The sealing ring 118 is covered with a correspondingly sized and shaped ring of a layer of release paper 119 or other such suitable material to prevent contamination of the adhesive material prior to use.

A flexible ring 120 of generally open cell foam material is disposed within the internal chamber 104 of the shell 102. The ring 120 is bonded directly onto the interior surface of the bottom wall 112 surrounding opening 106 using a suitable adhesive. By way of example, the ring is approximately three-quarters of an inch thick and can be constructed of such materials as polyurethane foam which is conformable to the shape of the surface to which it is applied. Open cell polyurethane foam is characterized by a 1.4 pound density, a 34 pound indent load deformation, and is also fire retardant. The inner surface 121 of the ring 120 may be rendered impermeable to gas by coating with a sprayable vinyl material. In the alternative, the ring 120 may be constructed from a closed cell foam material to provide gas impermeability. The function of the ring 120 in the treatment of a patient will be described hereinafter.

Figure 3:
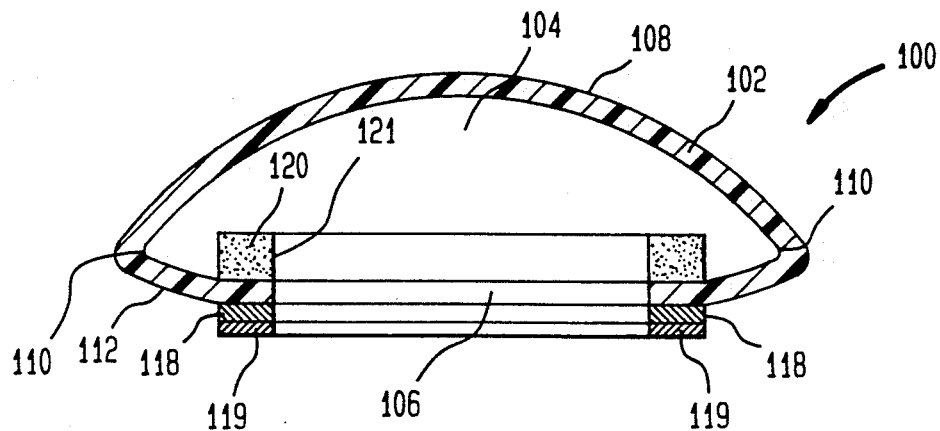
FIG. 3 is a cross-sectional view of the topical hyperbaric chamber taken along line 2—2 in FIG. 1, showing the hyperbaric chamber in a fully inflated configuration for therapeutically treating wounds and lesions of a patient.

As a result of the shell 102 being constructed from resilient plastic material, the shell is collapsible, to assume a flat configuration as shown in FIG. 2. As a result of the collapsibility of the shell 102, the hyperbaric chamber 100 will occupy a substantially smaller storage space than one when configured in its fully expanded configuration as shown in FIG. 3. For example, it is estimated that the shell 102 will be approximately six to ten times smaller in maximum height when collapsed than when fully expanded. This can result in substantial savings in shipping costs over certain known hyperbaric chambers such as the prior Loori chamber which is constructed from noncollapsible polyurethane foam.

Referring now to FIGS. 3 through 6, the application of the hyperbaric chamber 100 to a patient's body for the treatment of various wounds and lesions will now be described. The adhesive sealing ring 118, in conjunction with internal chamber 104, when applied to the patient's body creates an encapsulated area except for the passageways provides by gas inlet tube 114 and pressure relief tube 116. In use, gas inlet tube 114 is sealed by attachment to a therapeutic gas source 122 and pressure relief tube 116 is sealed by attachment to pressure release apparatus 124.

In a preferred embodiment of the present invention, shell 102 in its fully collapsed configuration as shown in FIG. 2, in conjunction with adhesive sealing ring 118 after removal of the release paper 119, is affixed to the patient's body so as to encapsulate within the opening 106 a treatable wound or lesion. The ring 120 effectively maintains the top member 108 where it overlies the opening 106 spaced from the patient's body when the shell 102 is in its fully collapsed configuration. This prevents the top wall 108 from touching the wound or lesion to be treated, which might otherwise cause additional irritation. As the shell 102, in particular bottom member 112, is constructed of flexible plastic material, an effective seal can be attained around the wound or lesion despite the presence of an irregularly shaped surface. The ring 120 facilitates the ability to squeeze and conform the adhesive sealing ring 118 into the gluteal fold of the patient and to maintain an effective hermetic seal thereat. The hyperbaric chamber 100, as shown, is affixed to the lower back in the region of the upper buttocks. The hyperbaric chamber 100 is secure to the patient by means of an H-shaped belt 126 whose construction is more fully disclosed in FIG. 5.

The belt 126 includes a pair of spaced apart elongated strips 128, 130 having velcro-like material 132 provided on their free ends. A pair of cross-strips 134, 136 are secured in spaced apart parallel relationship transversely to the elongated strips 128, 130. As a result of this H-shaped construction, an opening 138 is provided between the cross-strips 134, 136. The elongated strips 128, 130 and cross-strips 134, 136 can be constructed from any suitable material, such as nylon, which in addition to being strong and durable, is also washable.

Figure 4:
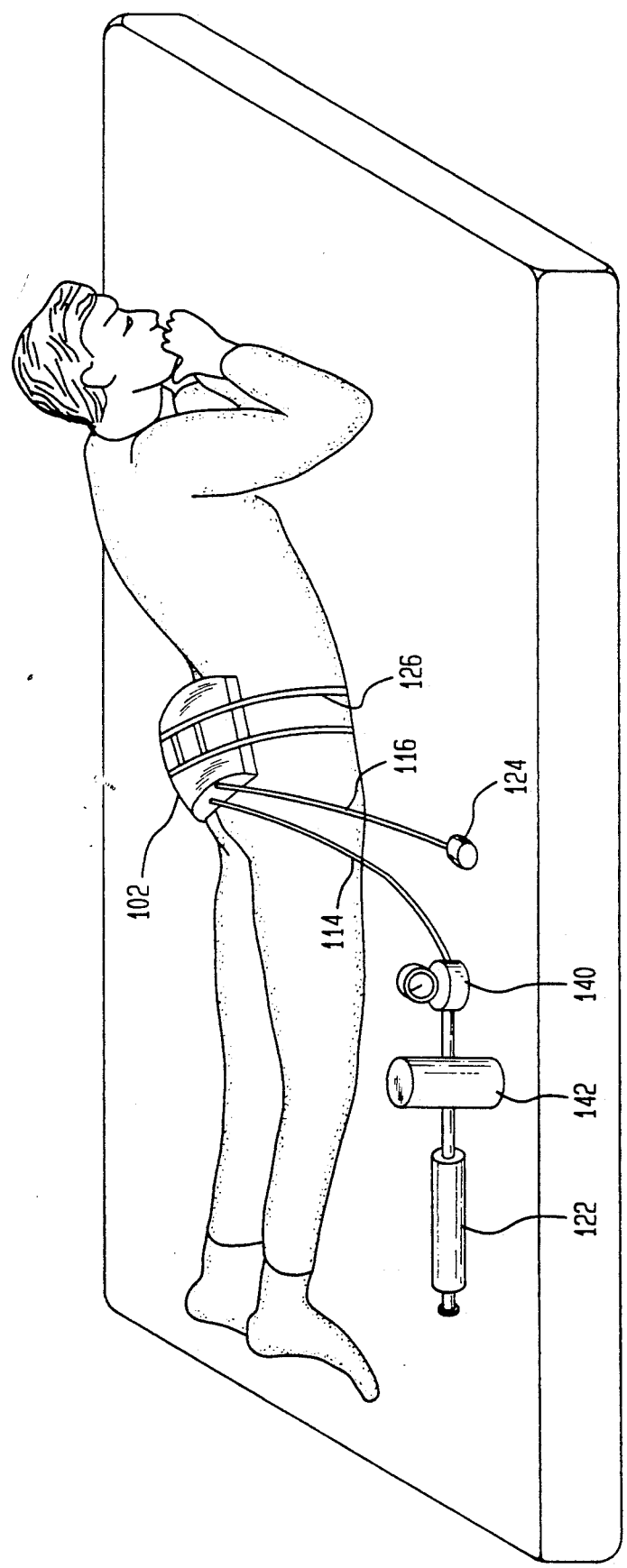
FIG. 4 illustrates a perspective and diagrammatic view of the topical hyperbaric chamber constructed in accordance with the present invention applied to a patient to receive treatment.
Figure 5:
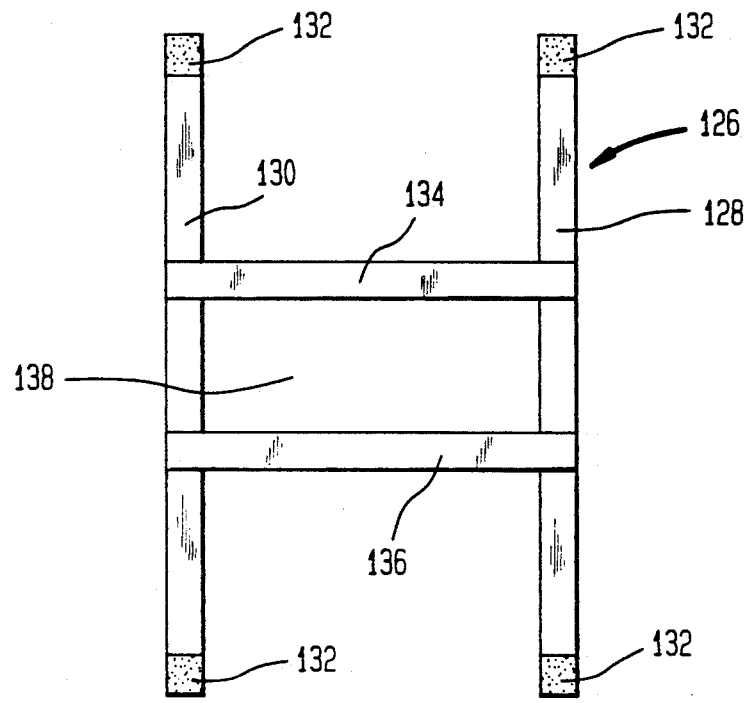
FIG. 5 is a top plan view of a strap constructed for removably securing the topical hyperbaric chamber about a portion of a patient's body.
Figure 6:
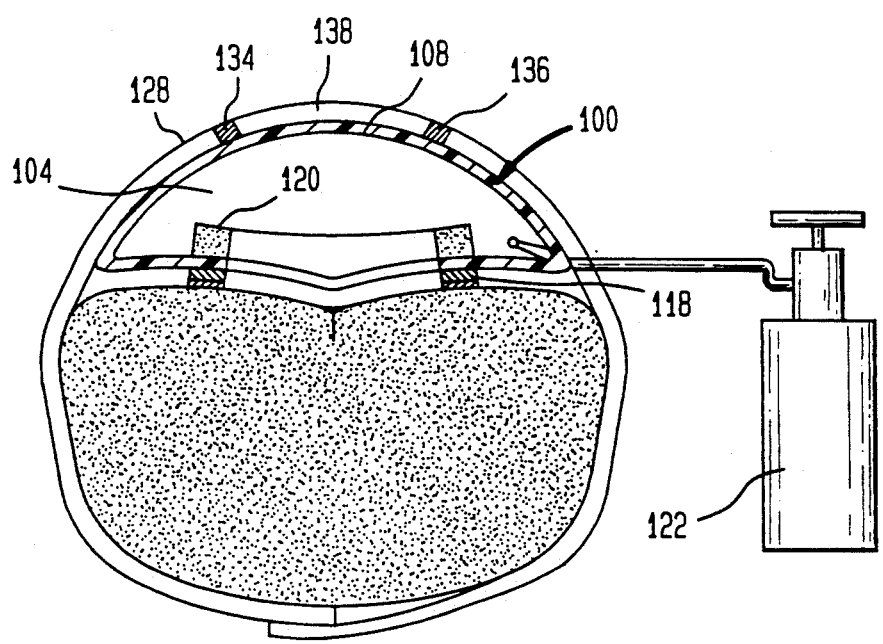
FIG. 6 is a side elevational view, in partial cross-section, of the topical hyperbaric chamber constructed in accordance with the present invention and disposed on an irregular shaped surface of a patient's body illustrating the chamber's ability to surface conform thereto in creating a hermetic seal.

In securing the hyperbaric chamber 100 to the body of a patient, the belt 126 is positioned, as shown in FIGS. 4 and 6, with opening 138 centrally overlying the top member 108 of shell 102. This permits visual viewing of the patient's wounds or lesions through the clear top member 108 of the shell 102. The elongated strips 128, 130 are wrapped around the patient's body and adhere to one another at their ends using the velcro-like material 132.

Therapeutic gases from the gas source 122 are supplied to the internal chamber 104 of the shell 102 through a pressure regulator 140 and optionally a humidification device 142. Pressure relief apparatus 124 will ensure that the optimal conditions are maintained within the internal chamber 104. In accordance with one embodiment, the pressure relief apparatus 124 is a static pressure relief valve.

As therapeutic gases from the gas source 122 are supplied to the hyperbaric chamber 100, the gas pressure within the interior chamber 104 of the shell 102 begins to increase thereby inflating the shell to its fully expanded configuration as shown in FIG. 3. As the shell 102 is constructed from heat sealed plastic material, higher pressures are attainable than in the prior known chambers. For example, operating pressures in the range of 39 to 52 mmHg are typical, although higher pressures are attainable, while the prior known chambers were limited in the range of about 39 mm Hg due to leakage.

Figure 7:
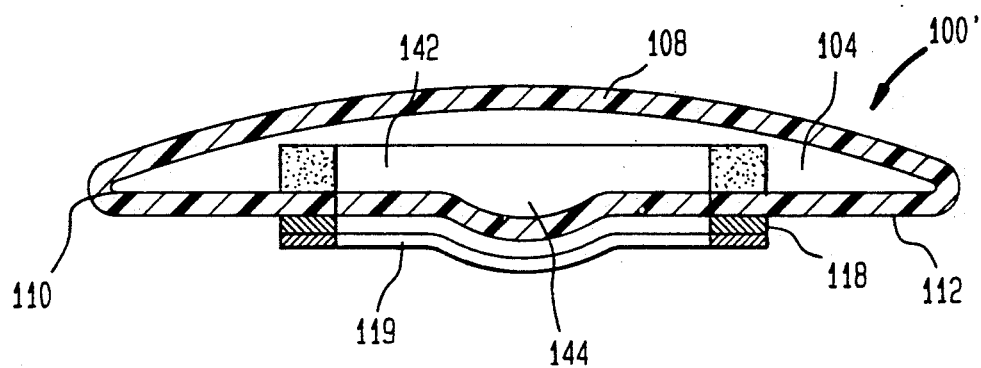
FIG. 7 is a cross-sectional view of a topical hyperbaric chamber constructed in accordance with another embodiment of the present invention to facilitate the formation of a hermetic seal in the region of the gluteal fold of the patient.

Referring now to FIG. 7, there is shown a topical hyperbaric chamber 100' in accordance with another embodiment of the present invention. The hyperbaric chamber 100' is differentiated from the hyperbaric chamber 100 of FIG. 2 in the construction of the flexible ring 142. In this regard, the ring 142 is provided at one circumferential position with a protuberance 144 having a bell-shaped profile. In accordance with one embodiment, the height of the protuberance 144 above the surrounding surface of the ring 142 is approximately one inch while its width at the base of the protuberance is approximately an inch and a half. The protuberance 144 results in the adhesive sealing ring 118 being deformed into a corresponding bell-shape as the protuberance deforms the bottom member 112 outwardly as shown.

The protuberance 144 facilitates creating and maintaining of a hermetic seal by the adhesive sealing ring 118 in the area of the gluteal fold of the patient's body. In this regard, it is frequently known that lesions and other wounds to be treated are formed adjacent the gluteal fold of the patient. The portion of the adhesive sealing ring 118 being distorted by the protuberance 144 is positioned over the gluteal fold and squeezed therein via the assistance of the protruding protuberance 144. The protuberance 144 presses the adhesive sealing ring 118 into the gluteal fold and maintains this position to create a hermetic seal during treatment using the hyperbaric chamber 100'. Typically, the provision of a single protuberance 144 is sufficient as it is not usually the occasion that the hyperbaric chamber 100' would be positioned overlying the entire extent of the gluteal fold. However, it is contemplated that a flexible ring 142 provided with two opposing protuberances 144 may be employed if desired.

The collapsible construction of the hyperbaric chamber 100 has a substantial benefit in reducing shipping costs, as well as storage space requirements. This results in lower costs which will enable a wider distribution of the hyperbaric chamber 100 to remote and foreign markets. Further, the construction of the hyperbaric chamber 100 from plastic material, renders the apparatus both low cost and washable. There has been a significant need for a disposable hyperbaric chamber 100 in multi-patient health care facilities. In such facilities, there exists a considerable handicap in the use of hyperbaric chambers, namely, between each use, the device necessarily requires sterilization. Further, there is always the risk of spreading the contagion of an infectious disease. As a result, the hyperbaric chamber 100 may be economically disposed of after patient use. In addition, as certain patients may be incontinent, the hyperbaric chamber 100 is fully washable, as well as belts 126, to maintain a clean and/or sterile environment during individual patient use.

Figure 8:
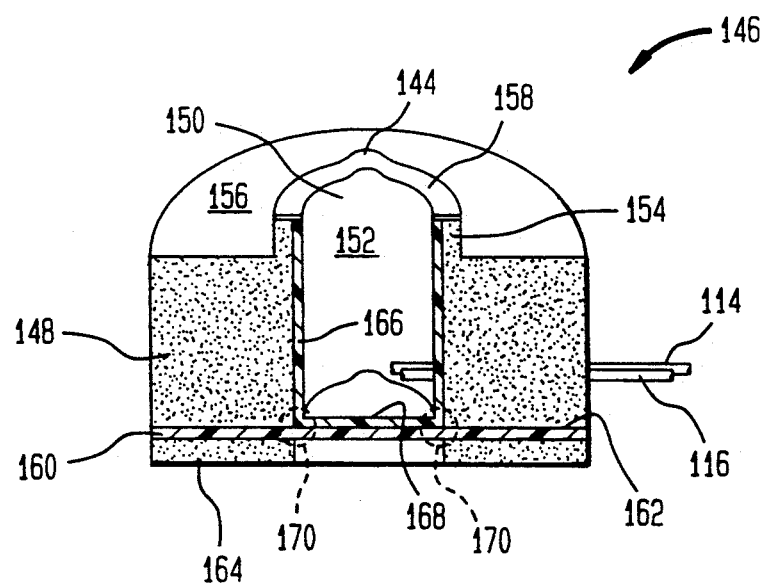
FIG. 8 is a perspective cross-sectional view of a topical hyperbaric chamber constructed in accordance with another embodiment of the present invention.

Referring now to FIG. 8, there is shown a topical hyperbaric chamber 146 constructed in accordance with another embodiment of the present invention. The hyperbaric chamber 146 is generally constructed as a modified form of the hyperbaric chamber disclosed in Loori, U.S. Pat. No. 4,801,291. The hyperbaric chamber 146 includes a first annular shell 148 having an opening 150 extending therethrough to form an internal chamber 152. A projecting annular ring 154 is formed integral with the shell 148 extending outwardly from the top surface 156 surrounding the opening 150. The ring 154 is provided with a protuberance 144 as previously described and is covered with an adhesive layer 158, as well as a layer of release paper (not shown). A sheet 160 of transparent material, such as resilient plastics including vinyl materials is adhesively bonded across the bottom surface 162 of the shell 148 and overlying the opening 150. A second annular shell 164 is adhesively bonded to the sheet 160 about opening 150. As thus far described, except for the provision of the protuberance 144, the hyperbaric chamber 146 is of similar construction to that disclosed in the aforementioned Loori patent.

In the chamber of the prior Loori patent, a tubular gas impermeable liner open at both ends was inserted within the opening 150 and adhesively bonded circumferentially at its free end to sheet 160. This construction, however, often resulted in leakage of the pressurized treatment gas through the adhesively bonded sealed area. In accordance with the present invention, there is provided a gas impermeable liner 166 in the nature of a closed ended cylindrical tube having a bottom wall 168. The liner 166 is heat sealed about its closed periphery to the sheet 160 in the area designated by the dashed circles 170. As a result of this construction, the internal chamber 152 of the hyperbaric chamber 146 may be pressurized to greater treatment pressures without leakage as was the previous case in the known hyperbaric chamber. In addition, the provision of a protuberance 144 on ring 154 enhances the formation of a hermetic seal on irregular shaped surfaces of a patient's body, in particular, within the gluteal fold.

Although the invention herein has been described with references to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

What is claimed is:

1. A topical hyperbaric chamber comprising a shell defining a substantially closed internal chamber arrangable between an expanded and collapsed configuration, said shell having an opening therethrough communicating with said internal chamber, a ring within said internal chamber secured to said shell about said opening, said shell about said opening capable of conforming to a shaped surface of a patient's body, and gas introducing means for introducing therapeutic gases into the internal chamber for expanding said shell from a collapsed to an expanded configuration and therapeutically treating a portion of a patient's body exposed within the opening.

2. The topical hyperbaric chamber according to claim 1 wherein said shell is constructed of flexible plastic material.

3. The topical hyperbaric chamber according to claim 1 wherein said shell includes a top member opposing said opening, said top member being constructed of transparent material.

4. The topical hyperbaric chamber according to claim 1 wherein the volume of said internal chamber of said shell when in said expanded configuration is substantially greater than the volume of said internal chamber when said shell is in said collapsed configuration.

5. The topical hyperbaric chamber according to claim 1 wherein said ring is sufficiently flexible so as to be capable of conforming to an irregularly shaped surface of a patient's body.

6. The topical hyperbaric chamber according to claim 1 wherein said opening is of a predetermined size sufficient to encompass the portion of the patient's body to be treated.

7. The topical hyperbaric chamber according to claim 1 further including means adapted to be applied to the patient's body for positioning said shell.

8. The topical hyperbaric chamber according to claim 7 wherein said means comprises a belt constructed from a pair of spaced elongated side strips and a pair of spaced cross strips attached to said side strips, said cross strips forming an opening therebetween.

9. The topical hyperbaric chamber according to claim 8 further including fastening means attached to the opposite ends of said elongated side strips to enable releasably securing the opposing ends together.

10. The topical hyperbaric chamber according to claim 8 wherein said opening between said cross strip is of a predetermined size sufficient to enable viewing of that portion of the patient's body being treated within said opening of said shell.

11. The topical hyperbaric chamber according to claim 1, further including adhesive sealing means provided on the external surface of said shell about said opening for adhesively sealing said shell to a patient's body about the portion to be treated.

12. The topical hyperbaric chamber according to claim 11 wherein said adhesive sealing means is comprised of an adhesive polymer resin.

13. The topical hyperbaric chamber according to claim 1, wherein said ring includes a protuberance extending outwardly of said internal chamber.

14. The topical hyperbaric chamber according to claim 13, wherein said protuberance has a bell-shaped profile.

15. The topical hyperbaric chamber according to claim 1, wherein said ring has an outside diameter substantially less than an inside diameter of a bottom member forming said shell to which said ring is secured.

16. A topical hyperbaric apparatus comprising a shell defining a substantially enclosed internal chamber arrangeable between an expanded and collapsed configuration, said shell having an opening therethrough communicating with said internal chamber, sealing means about said opening for sealing said shell to a patient's body about a portion to be treated, a ring within said internal chamber secured to said shell about said opening, said ring being sufficiently flexible so as to be capable of conforming to an irregularly shaped surface of a patient's body, and gas introducing means for introducing therapeutic gases into said internal chamber for expanding said shell from a collapsed to an expanded configuration and therapeutically treating the portion of the patient's body exposed within said opening.

17. The topical hyperbaric apparatus according to claim 16 wherein said shell is constructed of flexible plastic material.

18. The topical hyperbaric apparatus according to claim 16 wherein said shell includes a top member opposing said opening, said top member being constructed of transparent material.

19. The topical hyperbaric apparatus according to claim 16 wherein the volume of said internal chamber of said shell when in said expanded configuration is substantially greater than the volume of said internal chamber when said shell is in said collapsed configuration.

20. The topical hyperbaric apparatus according to claim 16 of wherein said ring is constructed foam material.

21. The topical hyperbaric apparatus according to claim 16 wherein said ring includes a protuberance extending outwardly.

22. The topical hyperbaric apparatus according to claim 21 wherein said protuberance has a bell-shaped profile.

23. The topical hyperbaric apparatus according to claim 16 further including a belt adapted to be applied to the patient's body for positioning said shell, said belt constructed from a pair of spaced elongated side strips and a pair of spaced apart cross strips attached to said side strips, said cross strips forming an opening therebetween.

24. The topical hyperbaric apparatus according to claim 16, wherein said sealing means comprises an adhesive provided on the external surface of said shell about said opening for adhesively sealing said shell to a patient's body about the portion to be treated.

25. The topical hyperbaric apparatus according to claim 16 wherein said ring has an outside diameter substantially less than an inside diameter of a bottom member forming said shell to which said ring is secured.

26. A topical hyperbaric chamber comprising a shell defining a substantially closed internal chamber arrangable between an expanded and collapsed configuration, said shell having an opening therethrough communicating with said internal chamber, means within said internal chamber secured to said shell about said opening for maintaining a portion of said shell overlying said opening spaced therefrom when said shell is in a collapsed configuration, said shell about said opening capable of conforming to a shaped surface of a patient's body, and gas introducing means for introducing therapeutic gases into the internal chamber for expanding said shell from a collapsed to an expanded configuration and therapeutically treating a portion of a patient's body exposed within the opening.

27. The topical hyperbaric chamber according to claim 26 further including adhesive sealing means provided on the external surface of said shell about said opening for adhesively sealing said shell to a patient's about the portion to be treated.

28. The topical hyperbaric chamber according to claim 26 wherein said means comprises a ring secured to the internal surface of said shell about said opening.

29. The topical hyperbaric chamber according to claim 28 wherein said ring includes a protuberance extending outwardly of said internal chamber.

30. The topical hyperbaric chamber according to claim 29 said protuberance has a bell-shaped profile.

31. The topical hyperbaric chamber according to claim 28 wherein said ring has an outside diameter substantially less than an inside diameter of a bottom member forming said shell to which said ring is secured.

32. A method of treating medical irregularities on a patient's body comprising providing a shell defining a substantially enclosed internal chamber arrangable between an expanded and collapsed configuration, said shell having an opening therethrough communicating with said internal chamber and surrounding a portion of the patient's body to be treated and a ring within said internal chamber secured to the internal surface of said shell about said opening, affixing said shell to a patient's body about said opening by an adhesive layer provided on the external surface of said shell and by conforming said ring to a shaped surface of the patient's body, maintaining a portion of said shell overlying said opening a spaced distance therefrom by supporting said shell upon said ring when affixing said shell in said collapsed configuration to a patient's body, and introducing therapeutic gases into said internal chamber for expanding said shell from the collapsed to the expanded configuration and therapeutically treating the portion of the patient's body exposed within said opening.

* * * * *

UNITED STATES PATENT AND TRADEMARK OFFICE
CERTIFICATE OF CORRECTION

PATENT NO. : 5,154,697

DATED : October 13, 1992

INVENTOR(S) : Loori

It is certified that error appears in the above-identified patent and that said Letters Patent is hereby corrected as shown below:

Column 5, line 48, delete "!02" and insert therefor --102--.

Column 10, line 47, after "16", delete "of".

Column 11, line 26, before "about", insert --body--.

Column 12, line 5, after "29", insert --wherein--.

Signed and Sealed this

Second Day of November, 1993

Attest:

BRUCE LEHMAN

Attesting Officer

Commissioner of Patents and Trademarks